United States Patent [19]

Senaratne

[11] Patent Number: 5,710,340
[45] Date of Patent: Jan. 20, 1998

[54] SYNTHESIS OF CYCLOALKYLDIARYLPHOSOPHINES

[75] Inventor: K. Pushpananda A. Senaratne, Baton Rouge, La.

[73] Assignee: Albemarle Corporation, Richmond, Va.

[21] Appl. No.: 639,497

[22] Filed: Apr. 29, 1996

[51] Int. Cl.$^6$ .................................................. C07F 9/50
[52] U.S. Cl. .................................................. 568/17
[58] Field of Search .................................................. 568/17

[56] References Cited

U.S. PATENT DOCUMENTS

| | | |
|---|---|---|
| 2,902,517 | 9/1959 | Schmerling. |
| 4,618,720 | 10/1986 | Bay .................................................. 568/17 |
| 4,668,823 | 5/1987 | Murray .................................................. 568/17 |
| 5,288,912 | 2/1994 | Devon .................................................. 568/17 |

OTHER PUBLICATIONS

Aguiar et al., "Lithium Diphenylphosphide: A Convenient Source and Some Reaction", JOC Mar. 1962, vol. 27, pp. 1001–1004.

Toth et al., "Aspects of the Cleavage of Phosphines with Potassium: Synthesis and Reactivity of Lithium and Potassium Bis(p-(dimethylamino)phenyl)phosphide", Organometallics 1990, vol. 9, No. 3, pp. 675–680.

Rossi et al., "Reaction of 1-Bromoadamantane with Diphenylphosphide and Diphenylarsenide Ions by the SRN1 Mechanism. Facile Nucleophilic Substitution at the Bridgehead Position", J Org Chem 1982, vol. 47, No. 24, pp 4654–4657.

Aguiar et al., "The Reaction of Lithium Diphenyphosphide and Simple Aryl Halides", Aug. 1963, vol. 28, pp 2091–2093.

Tsvetkov et al., "A Simple Synthesis and Some Synthetic Applications of Substituted Phosphide and Phosphinite Anions", Synthesis, Mar. 1986, pp. 198–208.

Hayashi et al., "Catalytic Asymmetric Hydroformylation by the Use of Rhodiumcomplexes of Chiral Bidentate Phosphorus Ligands Bearing Saturated Ring Skeletons", Sep. 1979, Bulletin of the Chemical Society of Japan, vol. 52, No 9, pp 2605–2608.

Morrison et al., "Synthesis of Menthyl–and Neomenthydiphenylphosphine. Epimeric, Chiral, Tertiary Phosphine Ligands for Asymmetric Synthesis", J Org Chem, vol 39, No 2, 1974, pp. 270–272.

Wittenberg and Gilman, "Lithium Cleavages of Triphenyl Derivativess of Some Group Vb Elements in Tetrahydrofuran", J Org Chem vol 23, pp. 1063–1065, Jul. 1958.

Kuchen and Buchwald, "Reactions of diphenylphosphine Sodium", Angew Chem 69, pp 307–308 (1957)–Abstract Attached.

*Primary Examiner*—José G. Dees
*Assistant Examiner*—Jean F. Vollano
*Attorney, Agent, or Firm*—Philip M. Pippenger

[57] ABSTRACT

Phosphines having two aryl groups and one alkyl-substituted cycloalkyl group bonded to a phosphorus atom are formed by reacting an alkali metal diarylphosphide with a monoalkyl- or polyalkyl-substituted cycloalkyl mesylate or tosylate in which an alkyl group is in the 2-position, in a liquid reaction medium in which these reactants are soluble. This process avoids complications associated with prior known process technology for producing such phosphines. The phosphines are useful as ligands for making noble metal catalysts.

35 Claims, No Drawings

1
SYNTHESIS OF CYCLOALKYLDIARYLPHOSPHINES

TECHNICAL FIELD

This invention relates to an efficacious process for producing cycloalkyldiarylphosphines from triarylphosphines.

BACKGROUND

Cycloalkyldiarylphosphines constitute a group of chemical products of considerable usefulness as ligands for making noble metal catalysts. Menthyldiphenylphosphine and neomenthyldiphenylphosphine are examples of ligands which impart to transition metal complexes the potential for diastereomeric interactions with unsaturated organic substrates, thus making asymmetric synthesis possible. Note in this connection, J. D. Morrison and W. F. Masler, *J. Org. Chem.*, 1974, Vol. 39, No. 2, pages 270–272. Neomenthyldiphenylphosphine is of particular importance for the preparation of noble metal catalysts useful in the synthesis of certain pharmaceuticals such as naproxen, ketoprofen, ibuprofen, etc.

A known method of generating tertiary phosphines with two aryl groups and a dissimilar third hydrocarbyl group involves coupling a lithium diaryl phosphide with a halohydrocarbon such as benzyl chloride in an ether such as tetrahydrofuran. See A. M. Aguiar, J. Beisler and A. Mills, *J. Org. Chem.*, 1962, Vol. 27, pages 1001–1005. Because the reaction co-produces a reactive aryl lithium coproduct which can complicate synthesis procedures, the authors (Aguiar et al.) developed a method of selectively eliminating this coproduct. They accomplished this by adding to the reaction mass an equivalent amount of tert-butyl chloride to selectively react with the aryl lithium so that isobutylene, aromatic hydrocarbon and lithium chloride are formed. Nevertheless an extra reactant and a concurrent reaction were involved in this approach.

Another complicating factor in the reaction of lithium diaryl phosphide with a halohydrocarbon in tetrahydrofuran is that one or more components in the system tend to interact with the tetrahydrofuran whereby side reactions such as ring cleavage can occur under the conditions used. In addition, the reaction between lithium diaryl phosphide and menthyl chloride is slow giving low to moderate yields, and requires prolonged reaction periods, which in turn favors the opportunity for more adverse interaction with the cyclic ether solvent such as ring cleavage to occur.

SUMMARY OF THE INVENTION

In accordance with this invention, a new, highly efficacious process for the production of tertiary phosphines having two aryl groups and one alkyl-substituted cycloalkyl group is provided. This new process avoids complications associated with the prior known process technology referred to above.

Pursuant to one embodiment of this invention, an alkali metal diarylphosphide is reacted with a monoalkyl- or polyalkyl-substituted cycloalkyl mesylate or tosylate in which an alkyl group is in the 2-position, in a suitable liquid reaction medium in which these reactants are soluble, such that a diaryl monoalkyl- or polyalkyl-substituted cycloalkyl tertiary phosphine is formed. Unlike the known process involving use of a chloro-substituted reactant to introduce a third group to form the tertiary phosphine, the present process eliminates the possibility of a competitive reaction between a chloro-substituted reactant and the coproduced aryl lithium as it is formed. Thus this invention makes possible improvements both in yield and quality of the diaryl monoalkyl- or polyalkyl-substituted cycloalkyl tertiary phosphine product.

In another of its embodiments this invention provides a two-stage process of forming a tertiary phosphine having two aryl groups and one monoalkyl- or polyalkyl-substituted cycloalkyl group. This process comprises:

a) reacting a monoalkyl- or polyalkyl-substituted cycloalkanol in which an alkyl group is in the 2-position with a mesyl halide or tosyl halide in a liquid reaction medium in which these reactants are soluble, to form a monoalkyl- or polyalkyl-substituted cycloalkyl mesylate or tosylate; and b) reacting at least a portion of said mesylate or tosylate with an alkali metal diarylphosphide, in a liquid reaction medium in which these reactants are soluble, such that said phosphine is formed.

Still another embodiment of this invention is a three-stage process for producing a diaryl monoalkyl- or polyalkyl-substituted cycloalkyl tertiary phosphine. In this case the process comprises the following steps:

a) reacting an alkali metal with a triaryl phosphine in a liquid reaction medium in which the phosphine is soluble, to form an alkali metal diaryl phosphide;

b) reacting a monoalkyl- or polyalkyl-substituted cycloalkanol in which an alkyl group is in the 2-position with a mesyl halide or tosyl halide in a liquid reaction medium in which these reactants are soluble, to form a monoalkyl- or polyalkyl-substituted cycloalkyl mesylate or tosylate; and c) reacting at least a portion of said mesylate or tosylate with at least a portion of said alkali metal diarylphosphide, in a liquid reaction medium in which these reactants are soluble, such that a tertiary phosphine having two aryl groups and one monoalkyl- or polyalkyl-substituted cycloalkyl group is formed.

In each of the above embodiments the term "soluble" means that the reactant specified as being soluble is capable of dissolving in the liquid reaction medium at the reaction temperature being employed, at least to the extent necessary to enable the reaction to proceed at a reasonable reaction rate. The term does not imply that the particular reactant must be soluble in all proportions, but in general the greater its solubility in the reaction medium, the better.

Among the features of this invention is that the reaction takes place without need for any catalyst. Thus use of a catalyst in the reaction is completely optional or discretionary. If use of a catalyst is desired, one may employ a catalytic amount of a tertiary amine as catalyst.

Other embodiments and features of this invention will be still further apparent from the ensuing description and appended claims.

FURTHER DESCRIPTION OF THE INVENTION

Alkali Metal Diarylphosphide (MDAP)

The alkali metal diarylphosphide used in the processes of this invention can be represented by the formula

where $R^1$ and $R^2$ are the same or different aryl groups, which will typically contain up to about 24 carbon atoms each. The aryl groups may have a single ring or a plurality of rings, and include phenyl, 1-naphthyl, 2-naphthyl, 2-biphenylyl, 3-biphenylyl, 4-biphenylyl, acenaphthyl, phenanthryl, tetrahydronaphthyl, and like aromatic groups. The aryl groups can be substituted or unsubstituted, and when substituted can contain one or more substituents inert to metallic alkali metal (lithium, sodium, potassium, etc.) such as one or more: alkyl groups, alkenyl groups, hydrocarbyloxy groups, hydrocarbylthio groups, hydrocarbylcarbonyl groups, hydrocarbyloxyhydrocarbyl groups, dihydrocarbylamino groups, and heteroaromatic groups, and combinations of two or more of these. Preferably, the aryl groups are phenyl groups each of which is either unsubstituted or has up to 3 alkyl substituents having up to about 4 carbon atoms each. Phosphides in which the two aryl groups are the same are preferred, and most preferred is lithium diphenylphosphide, sodium diphenylphosphide, potassium diphenylphosphide, and mixtures of sodium diphenylphosphide and potassium diphenylphosphide.

Alkyl-Substituted Cycloalkyl Mesylate or Tosylate (ACM or ACT)

The monoalkyl- or polyalkyl-substituted cycloalkyl mesylate or tosylate are alkyl-substituted cycloalkanes having attached to the ring a mesylate ($CH_3SO_2O$—) or tosylate (p—$CH_3C_6H_4SO_2O$—) moiety, respectively. They are produced by reacting a suitably monoalkyl- or polyalkyl-substituted cycloalkanol in which an alkyl group is in the 2-position with a mesyl halide or tosyl halide in a liquid reaction medium in which these reactants are soluble, to form a monoalkyl- or polyalkyl-substituted cycloalkyl mesylate or tosylate. The cycloalkyl group of the mesylate or tosylate preferably has from 5 to 8 carbon atoms in the ring and has a linear or branched alkyl group of up to about 12 carbon atoms substituted on one of the ortho positions of the cycloalkyl ring relative to the mesylate or tosylate functionality. In addition to this required ortho-alkyl substitution, the cycloalkyl ring may contain other substituents which are innocuous in the sense that they will not impair or inhibit the desired reaction. While such additional substituents can be in any positions which do not unduly sterically hinder the mesylate or tosylate functional group, such substituents are preferably in the meta or para positions relative to the mesylate or tosylate functional group. Examples of such innocuous substituents include alkyl groups, alkenyl groups, hydrocarbyloxy groups, hydrocarbylthio groups, hydrocarbylcarbonyl groups, hydrocarbyloxyhydrocarbyl groups, and heteroaromatic groups, dihydrocarbylamino groups, and combinations of two or more of these. Typically in the practice of this invention, this reactant will contain a total of up to about 24 carbon atoms, and preferably up to about 18 carbon atoms, in the molecule. As regards cycloalkyl ring size, most preferably the ring is a 6-membered ring. The ortho-alkyl substituent is preferably a secondary alkyl group, which most preferably contains up to about 6 carbon atoms. Particularly preferred reactants are menthyl mesylate and menthyl tosylate.

Reaction Media

For the reaction between the alkali metal diarylphosphide and the monoalkyl- or polyalkyl-substituted cycloalkyl mesylate or tosylate, any suitably inert liquid reaction medium in which these reactants are soluble and that exists in the liquid state under the temperature conditions at which it is being used is suitable for use in the conduct of this reaction. Preferably the reaction medium should remain in the liquid state at 10° C. or below.

Thus, the reaction media may be composed of one or more ethers, hydrocarbons, ketones, tertiary amines, carboxylic acid esters, and/or other suitably inert liquids. Suitable ethers comprise monoethers and polyethers, and the ethers may be saturated or unsaturated, and they may be cyclic or acyclic, but in any case they should be free of any functionality that would interfere with or inhibit the desired reaction. Examples of polyethers include 1,2-dimethoxyethane, diglyme, 1,4-dioxane, tetrahydrofurfuryl ethyl ether, tetrahydrofurfuryl n-butyl ether, and similar polyethers. Preferably, the ether is one or more saturated hydrocarbyl monoethers, or one or more a hydrocarbyl monoethers having at least one aromatic group in the molecule. Examples include dialkyl ethers, dicycloalkyl ethers, diaryl ethers, monoalkyl monoaryl ethers, monocycloalkyl monoaryl ethers, monoalkyl monocycloalkyl ethers, and saturated cyclic monoethers, or mixtures of any of these. Particularly preferred are tetrahydrofuran and alkyl-substituted tetrahydrofurans.

It should be noted that lithium diarylphosphides tend to interact with ethers, especially cyclic ethers such as tetrahydrofuran and its alkyl congeners, presumably via a cleavage reaction. In contrast the sodium and potassium diarylphosphides do not exhibit this deleterious tendency to any appreciable extent. Thus when forming alkali metal diarylphosphide or employing an alkali metal diarylphosphide as a reactant in an ether reaction medium, especially in the particularly preferred tetrahydrofuran and alkyl-substituted tetrahydrofuran media, it is important to form or use (as the case may be) sodium diarylphosphide or potassium diarylphosphide, or a mixture of the two, rather than a lithium diarylphosphide. On the other hand, when forming and conducting the reaction with a lithium diarylphosphide, use of a hydrocarbon reaction medium, especially an alkylaromatic hydrocarbon reaction medium, is recommended.

If a hydrocarbon solvent is used, it can comprise aliphatic, cycloaliphatic or aromatic hydrocarbons, or mixtures of two or more of these types. Preferred as a class are liquid aromatic hydrocarbons which may contain one or more rings and when more than one ring is present, the rings may be condensed or non-condensed rings. There may be one or more alkyl substituent on an aromatic ring so long as the hydrocarbon exists in the liquid state under the conditions being used. Examples of suitable liquid aromatic hydrocarbons include benzene, toluene, xylenes, ethyl benzene, 1,2,3,4-tetrahydronaphthalene, and the like. The reaction medium may be composed of a single aromatic hydrocarbon such as toluene or butylbenzene, or it may be a mixture of alkylaromatic hydrocarbons such as a mixture of o-, m- and p-xylene, BTX, a mixture of toluene and ethylbenzene, or a mixture of m- and p-xylene and pentaethylbenzene. When using an alkylaromatic hydrocarbon solvent, it is preferable to ensure that at least 50 volume percent of the alkylaromatic used is composed of one or more liquid aromatic hydrocarbons, substantially the entire balance, if any, most preferably being one or more cycloaliphatic hydrocarbons (preferably predominantly or entirely cycloparaffinic hydrocarbons) and/or one or more aliphatic hydrocarbons (preferably predominantly or entirely paraffinic hydrocarbons). Small amounts of unalkylated aromatic hydrocarbons such as benzene, naphthalene and biphenyl may be present in the medium. For toxicological reasons, reasonable care should of course be exercised in minimizing exposure of personnel to aromatic hydrocarbons, especially those containing benzene.

Examples of other suitable inert solvents for use in forming the reaction medium include acetone, methylethylketone, cyclohexanone, 2-methylcyclohexanone, 3-methylcyclohexanone, 4-methylcyclohexanone, 2,5-dimethylcyclohexanone, triethylamine, tripropylamine, N,N-dimethylaniline, N-methylpyrrole, pyridine, 2-picoline, 3-picoline, 4-picoline, 2-ethylpyridine, 3-ethylpyridine, 2-ethylpyridine, 4-methoxypyridine, ethyl acetate, amyl acetate, benzyl acetate, ethyl propionate, ethyl propionate, butyl propionate, methyl hexanoate, diethyl oxalate, ethylbenzoate, and other similar materials. Mixtures of (a) two or more ketones, or of (b) two or more tertiary amines or of (c) two or more carboxylic esters, or of (d) one or more ketones with one or more tertiary amines, or of (e) one or more ketones with one or more carboxylic esters, or of (f) one or more tertiary amines with one or more carboxylic esters, or of (g) one or more ketones with one or more tertiary amines and with one or more carboxylic esters can be used. Likewise any individual solvent or mixture of solvents of the types referred to in this paragraph can be mixed with one or more ethers or with one or more hydrocarbons, or with a combination of one or more ethers and one or more hydrocarbons.

Conditions for Reaction between MDAP and ACM or ACT

The conditions for the reaction between the alkali metal diarylphosphide and the monoalkyl- or polyalkyl-substituted cycloalkyl mesylate or tosylate need not be severe. Temperatures in the range of between about 50° and about 100° C. will normally suffice. A preferred range is from about 60° to about 70° C. The reaction is preferably performed at atmospheric pressure, although this is not essential. For example, if using a solvent that has a boiling point below the reaction temperature selected for use in the process, the reaction should be performed under super-atmospheric pressure sufficient to keep the solvent in the liquid state. Likewise reduced pressure can be employed under suitable circumstances (e.g., use of a high boiling reaction medium, etc.). Proportions are not critical, but normally will be relatively close to equimolar, e.g., from about 1 to about 1.2 mols of the alkyl-substituted cycloalkyl mesylate or tosylate per mol of the alkali metal diarylphosphide. The reaction should be conducted under a dry inert atmosphere.

Two- and Three-Stage Processes—Production of ACM or ACT

As noted above, in certain embodiments of this invention the monoalkyl- or polyalkyl-substituted cycloalkyl mesylate (ACM) or tosylate (ACT) is produced by a liquid phase reaction of a suitably alkyl-substituted cycloalkanol with methane sulfonyl halide (mesyl halide) or p-tolylsulfonyl halide (tosyl halide). Upon completion of this reaction the ACM or ACT can then be reacted with alkali metal diarylphosphide (MDAP), preferably in the same reaction medium or at least in the same kind of separate reaction media, and most preferably in the same reaction vessel. An advantageous feature of this two-stage process is that the by-products of this reaction are organic in nature are thus are more readily disposed of (e.g., by combustion) than the inorganic waste products (e.g., zinc dihalide) formed when forming a monoalkyl- or polyalkyl-substituted cycloalkyl halide for reaction with the alkali metal diaryl phosphide to form the desired tertiary phosphine end product. Moreover, solvent from the second stage can be recycled to the first stage thereby reducing raw material costs, and size and costs of waste product disposal.

The cycloalkanol used in this reaction is a monoalkyl- or polyalkyl-substituted cycloalkanol in which an ortho-position relative to the hydroxyl group is substituted by a linear or branched alkyl group of up to about 12 carbon atoms. Preferably this alkyl substituent is a secondary alkyl group having up to about 6 carbon atoms. In addition to this required ortho-alkyl substitution, the cycloalkyl ring may contain other substituents which are innocuous in the sense that they will not impair or inhibit the desired reaction. For further details concerning innocuous substituents, reference should be made to the discussion presented above in connection with the monoalkyl- or polyalkyl-substituted cycloalkyl mesylate or tosylate reactants which are the products of the present reaction. The cycloalkanol ring itself preferably has from 5 to 8 carbon atoms, and most preferably 6 carbon atoms. Examples of suitable cycloalkanols include 2-isopropylcyclopentanol, 2-isopropylcyclohexanol, 2-isopropylcycloheptanol, 2-isopropylcyclooctanol, 2-sec-amylcyclopentanol, 2-sec-butylcyclohexanol, 2-ethylcycloheptanol, 2-methylcyclooctanol, 2-octyl-3-methylcyclopentanol, 2-decyl-4-sec-butylcyclohexanol, 2-dodecyl-5-ethylcycloheptanol, 2,6-dimethylcyclooctanol, 2,3,5-trimethylcyclooctanol, and their congeners. Menthol is a particularly preferred cycloalkanol for use in forming the mesylate or tosylate.

Preferably the mesyl halide or tosyl halide used is a chloride, but the bromides and iodides can be used.

The liquid reaction medium in which the reaction between the monoalkyl- or polyalkyl-substituted cycloalkanol and a mesyl halide or tosyl halide is conducted is one in which these reactants are soluble. A tertiary amine can be employed to complex with the hydrogen halide coproduct of the reaction.

Preferred solvents for use in forming the reaction medium for this reaction are ethers and hydrocarbons of the types described above. However ketones, tertiary amines and/or carboxylic acid esters or various mixed solvent systems such as described above can be used.

Temperatures for the reaction between the monoalkyl- or polyalkyl-substituted cycloalkanol and a mesyl halide or tosyl halide will usually fall within the range of about −10° C. to about 20° C. and preferably within the range of about 0° C. to about 5° C.

Reactant proportions in the conduct of this reaction pursuant to this invention are typically from about 1 to about 1.2 toyls of the mesyl halide or tosyl halide per tool of the alkyl-substituted cycloalkanol reactant.

Two—and Three Stage Processes—Formation of MDAP

In one of the embodiments of this invention, the alkali metal diarylphosphide reactant (MDAP) is formed by cleaving a triaryl phosphine with alkali metal in a suitable reaction medium such as a hydrocarbon and/or ether reaction medium, preferably an ether reaction medium. The ethers and hydrocarbon media can be as described above. It will be recalled from the above that if the MDAP being formed is a lithium diarylphosphide it is important to avoid use of an ether reaction medium that interacts appreciably with lithium diarylphosphide, and instead make use of some other suitable medium such as a hydrocarbon medium, preferably an alkylaromatic hydrocarbon medium.

Upon completion of the reaction between the alkali metal and the triarylphosphine, the resultant MDAP is then reacted with the monoalkyl- or polyalkyl-substituted cycloalkyl mesylate (ACM) or tosylate (ACT), preferably in the same reaction medium and most preferably in the same reaction vessel. This two-stage process constitutes another embodiment of this invention. In addition, and as pointed out above, ACM or ACT itself can be formed by the reaction between a monoalkyl- or polyalkyl-substituted cycloalkanol and a mesyl halide or tosyl halide as described above. Thus in another preferred embodiment all three reactions (preparation of alkali metal phosphide, preparation of the cycloalkyl mesylate or tosylate, and reaction of the alkali metal phosphide with the cycloalkyl mesylate or tosylate) can be carried out in the same kind or type of reaction media (preferably an ether such as tetrahydrofuran or alkyl-substituted tetrahydrofuran where the alkali metal is sodium and/or potassium) thereby minimizing or at least simplifying separation procedures and providing end product of enhanced purity. Solvent recycles can be utilized in these two- and three-stage processes of this invention.

The triaryl phosphine to be used as the starting material in the reaction with the alkali metal can have aryl groups which are the same or different and at least two of which correspond to $R^1$ and $R^2$ above. Thus the three aryl groups of the tertiary phosphine reactants used in the practice of this invention will typically contain up to about 24 carbon atoms each. For further details, the description of $R^1$ and $R^2$ given above should be referred to.

The alkali metal is preferably employed in a suitable high surface physical form such as in ribbon form or in small pieces or in a finely-divided state such as a dispersion in an inert liquid.

In conducting this cleavage reaction, the temperature will be maintained in the range of about 20° C. to about 80° C., and preferably in the range of about 40° C. to about 60° C. The reaction is conducted at atmospheric pressure as there is no particular advantage (or harm) in conducting the reaction at reduced or elevated pressures. The ratio of alkali metal to triaryl phosphine is preferably maintained in the range of about 2 to about 4 gram atoms of alkali metal per gram mol of triarylphosphine.

The following example is presented for the purposes of illustration and not limitation.

EXAMPLE

Preparation of Sodium Diphenylphosphide

A solution of triphenylphosphine (25 grams, 0.095 mol) in dry tetrahydrofuran (THF) (200 mL) is refluxed with freshly cut sodium (8.77 gram, 0.381 gram atom) under a nitrogen atmosphere for 15 hours. Sodium diphenylphosphide (NaDPP) is formed as a red solution. In a reaction performed in this manner, the conversion to NaDPP was >95%.

Preparation of Menthol Mesylate

Methane sulfonyl chloride (11.97 grams, 0.104 mol) is added dropwise into a cold solution of menthol (14.82 grams, 0.095 mol) and triethylamine (11.53 grams, 0.114 mol) in 20 mL of dry THF. Because the reaction is highly exothermic, the reaction vessel is cooled in an ice-bath to maintain the internal temperature at 0° to 5° C. The reaction is completed in about 15 minutes after the addition of the reagents, and a beige-colored precipitate is formed. To the mixture is added 50 mL of ice-cold water to quench the reaction. The organic layer is separated, washed with 20 mL of ice-cold brine, dried over anhydrous $Na_2SO_4$, and filtered. The filtrate can be used in the subsequent reaction without further purification. In a reaction conducted in this manner, the yield of menthyl mesylate was >95%.

Preparation of Neomenthyl Diphenyl Phosphine (NMDPP)

The NaDPP solution in THF is placed in a flame dried flask. To this is added 22.23 grams (0.095 mol) of menthyl mesylate, and the mixture is heated to 65° C. After 3 hours at this temperature, the reaction mass is cooled to room temperature and quenched with water. The organic layer is separated and distilled to remove the solvents. The crude product is then dissolved in refluxing anhydrous methanol and cooled to obtain neomenthyl diphenyl phosphine (NMDPP) as white crystals. In a run performed in this manner without optimization, the recovered yield of NMDPP was 80%.

One or more formulas are used herein for the purpose of clarification and to facilitate discussion. In this connection, it is to be understood and appreciated that the formula given for the alkali metal diarylphosphides, although depicted in ionic format, should not be construed as requiring ionization of the alkali metal diarylphosphides at any time during the conduct of the process. Rather, it is intended that the alkali metal diarylphosphides, and indeed the other specified reactants, are in whatever chemical form they assume or acquire when brought together in the solvent or reaction media and when under the conditions specified for the particular reaction.

Each and every publication referred to in any portion of this specification is fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process of forming a tertiary phosphine having two aryl groups and one alkyl-substituted cycloalkyl group, which process comprises reacting an alkali metal diarylphosphide with a monoalkyl- or polyalkyl-substituted cycloalkyl mesylate or tosylate in which an alkyl group is in the 2-position, in a liquid reaction medium in which these reactants are soluble, such that said phosphine is formed.

2. A process according to claim 1 wherein the reaction medium is at least predominantely an ether reaction medium in which the ether is at least one saturated hydrocarbyl monoether, or at least one hydrocarbyl monoether having at least one aromatic group in the molecule; and wherein the alkali metal of said alkali metal diarylphosphide is sodium or potassium or a combination of sodium and potassium.

3. A process according to claim 2 wherein said ether is a dialkyl ether, a diaryl ether, a monoalkyl monoaryl ether, or a saturated cyclic monoether.

4. A process according to claim 1 wherein said ether is (i) tetrahydrofuran or (ii) at least one alkyl-substituted tetrahydrofuran, or a mixture of (i) and (ii).

5. A process according to claim 1 wherein said cycloalkyl mesylate or tosylate has at least one additional alkyl group on the cycloalkyl ring.

6. A process according to claim 1 wherein said cycloalkyl mesylate or tosylate has a 6-membered ring and one additional alkyl group on the ring in the 5-position.

7. A process according to claim 1 wherein said diarylphosphide is reacted with a monoalkyl- or polyalkyl-substituted cycloalkyl mesylate in which an alkyl group is in the 2-position.

8. A process according to claim 7 wherein said mesylate is menthyl mesylate.

9. A process according to claim 7 wherein the aryl groups of the phosphide are the same aryl groups.

10. A process according to claim 7 wherein the aryl groups of the phosphide are both phenyl groups.

11. A process according to claim 1 wherein said diarylphosphide is reacted with a monoalkyl- or polyalkyl-substituted cycloalkyl tosylate in which an alkyl group is in the 2-position.

12. A process according to claim 11 wherein said tosylate is menthyl tosylate.

13. A process according to claim 11 wherein the aryl groups of the phosphide are the same aryl groups.

14. A process according to claim 11 wherein the aryl groups of the phosphide are both phenyl groups.

15. A process according to claim 1 wherein the alkali metal diarylphosphide is a sodium or potassium diphenylphosphide in which the phenyl group is either unsubstituted or has up to 3 alkyl substituents having up to about 4 carbon atoms each.

16. A process according to claim 15 wherein the reaction medium is composed at least predominantly of a saturated cyclic monoether, wherein said cycloalkyl mesylate or tosylate is a dialkylcyclohexyl mesylate or tosylate in which said alkyl group in the 2-position is a secondary alkyl group having up to about 6 carbon atoms, and the other alkyl group is in the 3, 4- or 5-position.

17. A process according to claim 16 wherein the ether is (i) tetrahydrofuran or (ii) at least one alkyl-substituted tetrahydrofuran, or a mixture of (i) and (ii).

18. A process according to claim 17 wherein the diarylphosphide is reacted with menthyl mesylate.

19. A process according to claim 18 wherein the alkali metal diarylphosphide is sodium diphenylphosphide or potassium diphenylphosphide, or a mixture thereof and wherein the ether is tetrahydrofuran.

20. A process of forming a tertiary phosphine having two aryl groups and one monoalkyl- or polyalkyl-substituted cycloalkyl group, which process comprises:
   a) reacting a monoalkyl- or polyalkyl-substituted cycloalkanol in which an alkyl group is in the 2-position with a mesyl halide or tosyl halide in a liquid reaction medium in which these reactants are soluble, to form a monoalkyl- or polyalkyl-substituted cycloalkyl mesylate or tosylate; and
   b) reacting at least a portion of said mesylate or tosylate with an alkali metal diarylphosphide, in a liquid reaction medium in which these reactants are soluble, such that said phosphine is formed.

21. A process according to claim 20 wherein the reaction of b) is carried out in at least a major amount of the liquid reaction medium used in a).

22. A process according to claim 20 wherein the liquid reaction media in a) and b) are predominantly ether reaction media, and wherein the alkali metal of said alkali metal diarylphosphide is sodium or potassium or a combination of sodium and potassium.

23. A process according to claim 22 wherein said cycloalkanol is menthol and wherein said ether reaction media consist essentially of (i) tetrahydrofuran or (ii) at least one alkyl-substituted tetrahydrofuran, or a mixture of (i) and (ii).

24. A process of forming a diaryl cycloalkyl tertiary phosphine having two aryl groups and one monoalkyl- or polyalkyl-substituted cycloalkyl group, which process comprises:
   a) reacting an alkali metal with a triaryl phosphine in a liquid reaction medium in which the triarylphosphine is soluble, to form an alkali metal diarylphosphide;
   b) reacting a monoalkyl- or polyalkyl-substituted cycloalkanol in which an alkyl group is in the 2-position with a mesyl halide or tosyl halide in a liquid reaction medium in which these reactants are soluble, to form a monoalkyl- or polyalkyl-substituted cycloalkyl mesylate or tosylate; and
   c) reacting at least a portion of said mesylate or tosylate with at least a portion of said alkali metal diarylphosphide, in a liquid reaction medium in which these reactants are soluble, such that said diaryl cycloalkyl phosphine is formed.

25. A process according to claim 24 wherein liquid reaction medium used in c) is recycled to a) or b), or to both a) and b).

26. A process according to claim 24 wherein the liquid reaction media in a), b) and c) are at least predominantly ether reaction media, and wherein the alkali metal of said alkali metal diarylphosphide is sodium or potassium or a combination of sodium and potassium.

27. A process according to claim 24 wherein the liquid reaction media in a), b) and c) are at least predominantly ether reaction media, wherein each of said reaction media is composed of substantially the same kind of ether or mixture of ethers as each of the other two said reaction media, and wherein the alkali metal of said alkali metal diarylphosphide is sodium or potassium or a combination of sodium and potassium.

28. A process according to claim 24 wherein the alkali metal is sodium or potassium, wherein the triaryl phosphine is triphenyl phosphine, wherein the cycloalkanol is a polyalkyl-substituted cyclohexanol, wherein the mesyl halide or tosyl halide is mesyl chloride or tosyl chloride, respectively, and wherein the liquid reaction media in a), b) and c) are at least predominantly ether reaction media.

29. A process according to claim 28 wherein polyalkyl-substituted cyclohexanol is menthol.

30. A process according to claim 29 wherein the menthol is reacted with mesyl chloride in (i) tetrahydrofuran or (ii) alkyl-substituted tetrahydrofuran, or a mixture of (i) and (ii).

31. A process of forming a diaryl cycloalkyl tertiary phosphine having two aryl groups and one monoalkyl- or polyalkyl-substituted cycloalkyl group, which process comprises:
   a) reacting an alkali metal with a triaryl phosphine in a liquid reaction medium in which the triarylphosphine is soluble, to form an alkali metal diarylphosphide; and
   b) reacting at least a portion of said alkali metal diarylphosphide with a monoalkyl- or polyalkyl-substituted cycloalkyl mesylate or tosylate in which an alkyl group is in the 2-position of the cycloalkyl group, in a liquid reaction medium in which these reactants are soluble, such that said diaryl cycloalkyl phosphine is formed.

32. A process according to claim 31 wherein the reaction of b) is carried out in at least a major amount of the liquid reaction medium used in a).

33. A process according to claim 31 wherein the liquid reaction media in a) and b) are ether reaction media, and wherein the alkali metal of said alkali metal diarylphosphide is sodium or potassium or a combination of sodium and potassium.

34. A process according to claim 33 wherein said ether reaction media consist essentially of (i) tetrahydrofuran or (ii) at least one alkyl-substituted tetrahydrofuran, or a mixture of (i) and (ii).

35. A process according to claim 34 wherein the triaryl phosphine is triphenyl phosphine and the mesylate or tosylate is menthyl mesylate or menthyl tosylate.

* * * * *